(12) United States Patent
Li

(10) Patent No.: US 11,345,893 B2
(45) Date of Patent: May 31, 2022

(54) ANTI-ROBO1 CAR-T CELL, AND PREPARATION AND APPLICATION THEREOF

(71) Applicant: ASCLEPIUS (Suzhou) TECHNOLOGY COMPANY GROUP CO., LTD., Suzhou (CN)

(72) Inventor: Huashun Li, Suzhou (CN)

(73) Assignee: Asclepius (Suzhou) Technology Company Group Co., Ltd., Suzhou (CN)

( * ) Notice: Subject to any disclaimer, the term of this patent is extended or adjusted under 35 U.S.C. 154(b) by 727 days.

(21) Appl. No.: 16/094,247

(22) PCT Filed: Jul. 31, 2016

(86) PCT No.: PCT/CN2016/092577
§ 371 (c)(1),
(2) Date: Oct. 17, 2018

(87) PCT Pub. No.: WO2017/181552
PCT Pub. Date: Oct. 26, 2017

(65) Prior Publication Data
US 2019/0127696 A1 May 2, 2019

(30) Foreign Application Priority Data

Apr. 18, 2016 (CN) .......................... 201610237593.2

(51) Int. Cl.
| | |
|---|---|
| C07K 14/705 | (2006.01) |
| C12N 5/0786 | (2010.01) |
| A61P 35/00 | (2006.01) |
| C12N 15/85 | (2006.01) |
| C12N 5/0783 | (2010.01) |
| C12N 15/62 | (2006.01) |
| A61K 38/17 | (2006.01) |
| C12N 5/10 | (2006.01) |

(52) U.S. Cl.
CPC ............ *C12N 5/0645* (2013.01); *A61K 38/17* (2013.01); *A61P 35/00* (2018.01); *C12N 5/0636* (2013.01); *C12N 5/10* (2013.01); *C12N 15/62* (2013.01); *C12N 15/85* (2013.01); *C12N 2740/15041* (2013.01); *C12N 2740/16043* (2013.01)

(58) Field of Classification Search
None
See application file for complete search history.

(56) References Cited

U.S. PATENT DOCUMENTS

| | | | | |
|---|---|---|---|---|
| 8,906,682 | B2 * | 12/2014 | June ..................... | A61K 38/177 435/372.3 |
| 10,494,434 | B2 * | 12/2019 | Riddell .................. | A61P 31/12 |
| 2017/0267756 | A1 * | 9/2017 | Riddell ............ | C07K 14/70521 |

FOREIGN PATENT DOCUMENTS

WO   WO 2012079000   *   6/2012

OTHER PUBLICATIONS

Nakayama et al., Structural features of interfacial tyrosine residue in ROBO1 fibronectin domain-antibody complex: Crystallographic, thermodynamic, and molecular dynamic analyses Protein Science Dec. 9, 2014 pp. 328-340.*
Dotti et al., Design and Development of Therapies using Chimeric Antigen Receptor-Expressing T cells Immunol Rev. Jan. 2014; pp. 1-35.*
11D5-3-CD8BBZ [synthetic construct] GenBank: QGQ63513.1 Sep. 1, 2021; pp. 1-2.*
abss.uspto.gov/abss4examiners/ abss. ABSS database search NCBI Blast search results for RID-JWMWG2T7016 Aug. 31, 2021; pp. 1-2.*
Guanghui et al., "Advances in Adoptive Cellular Immunotherapy for Cancer," Translational Medicine Journal, 4:4, (2015).

* cited by examiner

*Primary Examiner* — Maria G Leavitt
(74) *Attorney, Agent, or Firm* — Finnegan, Henderson, Farabow, Garrett & Dunner, LLP

(57) ABSTRACT

Provided is a method for modifying a chimeric antigen receptor-modified T cell (CAR-T cell). The method comprises expressing an SCFV-CDS TM-4-1BB-CD3ζ molecule in a T cell. The CAR-T cell prepared using the method can specifically recognize and bind to a tumor cell with elevated expression of a ROBO1 protein, and can be used to prevent and treat a corresponding tumor-related disease.

4 Claims, 2 Drawing Sheets

Specification includes a Sequence Listing.

SEQUENCE LISTING

<160> NUMBER OF SEQ ID NOS: 7

<210> SEQ ID NO 1
<211> LENGTH: 24
<212> TYPE: PRT
<213> ORGANISM: Homo Sapiens
<220> FEATURE:
<223> OTHER INFORMATION: SEQ ID NO:1 - Human

<400> SEQUENCE: 1

Ile Tyr Ile Trp Ala Pro Leu Ala Gly Thr Cys Gly Val Leu Leu
1               5                   10                  15

Ser Leu Val Ile Thr Leu Tyr Cys
            20

<210> SEQ ID NO 2
<211> LENGTH: 42
<212> TYPE: PRT
<213> ORGANISM: Homo Sapiens
<220> FEATURE:
<223> OTHER INFORMATION: SEQ ID NO:2 - Human

<400> SEQUENCE: 2

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 3
<211> LENGTH: 41
<212> TYPE: PRT
<213> ORGANISM: Homo Sapiens
<220> FEATURE:
<223> OTHER INFORMATION: SEQ ID NO:3 - Human

<400> SEQUENCE: 3

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 4
<211> LENGTH: 112
<212> TYPE: PRT
<213> ORGANISM: Artificial Sequence
<220> FEATURE:
<223> OTHER INFORMATION: SEQ ID NO:4 - Synthetic

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 236
<212> TYPE: PRT
<213> ORGANISM: Artificial Sequence
<220> FEATURE:
<223> OTHER INFORMATION: SEQ ID NO:5 - Synthetic

<400> SEQUENCE: 5

```
Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Asn Phe Leu
            20                  25                  30

Asn Trp Tyr Gln Gln Lys Pro Asp Gly Thr Val Lys Leu Leu Ile Tyr
        35                  40                  45

Tyr Thr Ser Arg Leu His Ser Gly Val Pro Ser Arg Phe Ser Gly Ser
    50                  55                  60

Gly Ser Gly Thr Asp Phe Ser Leu Thr Ile Ser Lys Leu Glu Gln Glu
65                  70                  75                  80

Asp Ile Ala Thr Tyr Phe Cys Gln Gln Gly Asn Thr Leu Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Leu Gln Gln Ser Gly Pro Glu
        115                 120                 125

Leu Val Lys Pro Gly Ala Ser Val Lys Ile Ser Cys Lys Ala Ser Gly
    130                 135                 140

Tyr Thr Phe Thr Asp Tyr Tyr Met Asn Trp Val Lys Leu Ser His Gly
145                 150                 155                 160

Lys Ser Leu Glu Trp Ile Gly Asp Ile Val Pro Asn Asn Gly Asp Thr
                165                 170                 175

Thr Tyr Asn Gln Asn Phe Arg Gly Lys Ala Thr Leu Thr Val Asp Lys
            180                 185                 190

Ser Ser Ser Thr Ala Tyr Met Glu Leu Arg Ser Leu Thr Ser Glu Asp
        195                 200                 205

Ser Ala Val Tyr Tyr Cys Ala Arg Phe Ser Asn Tyr Val Tyr Pro Phe
    210                 215                 220

Asp Tyr Trp Gly Gln Gly Thr Thr Ile Thr Val Ser
225                 230                 235
```

<210> SEQ ID NO 6
<211> LENGTH: 480
<212> TYPE: PRT
<213> ORGANISM: Artificial Sequence
<220> FEATURE:
<223> OTHER INFORMATION: SEQ ID NO:6 - Synthetic

<400> SEQUENCE: 6

```
Met Ala Leu Pro Val Thr Ala Leu Leu Leu Pro Leu Ala Leu Leu Leu
1               5                   10                  15

His Ala Ala Arg Pro Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Phe Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80
```

-continued

```
Arg Phe Ser Gly Ser Gly Ser Gly Thr Asp Phe Ser Leu Thr Ile Ser
                85                  90                  95

Lys Leu Glu Gln Glu Asp Ile Ala Thr Tyr Phe Cys Gln Gln Gly Asn
            100                 105                 110

Thr Leu Pro Leu Thr Phe Gly Ala Gly Thr Lys Leu Glu Leu Lys Gly
        115                 120                 125

Gly Gly Gly Ser Gly Gly Gly Ser Gly Gly Gly Ser Leu Gln
130                 135                 140

Gln Ser Gly Pro Glu Leu Val Lys Pro Gly Ala Ser Val Lys Ile Ser
145                 150                 155                 160

Cys Lys Ala Ser Gly Tyr Thr Phe Thr Asp Tyr Tyr Met Asn Trp Val
                165                 170                 175

Lys Leu Ser His Gly Lys Ser Leu Glu Trp Ile Gly Asp Ile Val Pro
            180                 185                 190

Asn Asn Gly Asp Thr Thr Tyr Asn Gln Asn Phe Arg Gly Lys Ala Thr
        195                 200                 205

Leu Thr Val Asp Lys Ser Ser Thr Ala Tyr Met Glu Leu Arg Ser
    210                 215                 220

Leu Thr Ser Glu Asp Ser Ala Val Tyr Tyr Cys Ala Arg Phe Ser Asn
225                 230                 235                 240

Tyr Val Tyr Pro Phe Asp Tyr Trp Gly Gln Gly Thr Ile Thr Val
                245                 250                 255

Ser Thr Thr Thr Pro Ala Pro Arg Pro Pro Thr Pro Ala Pro Thr Ile
                260                 265                 270

Ala Ser Gln Pro Leu Ser Leu Arg Pro Glu Ala Cys Arg Pro Ala Ala
            275                 280                 285

Gly Gly Ala Val His Thr Arg Gly Leu Asp Phe Ala Cys Asp Ile Tyr
290                 295                 300

Ile Trp Ala Pro Leu Ala Gly Thr Cys Gly Val Leu Leu Leu Ser Leu
305             310                 315                 320

Val Ile Thr Leu Tyr Cys Lys Arg Gly Arg Lys Lys Leu Leu Tyr Ile
                325                 330                 335

Phe Lys Gln Pro Phe Met Arg Pro Val Gln Thr Thr Gln Glu Glu Asp
            340                 345                 350

Gly Cys Ser Cys Arg Phe Pro Glu Glu Glu Glu Gly Gly Cys Glu Leu
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
    450                 455                 460

Thr Lys Asp Thr Tyr Asp Ala Leu His Met Gln Ala Leu Pro Pro Arg
465                 470                 475                 480

<210> SEQ ID NO 7
<211> LENGTH: 1439
<212> TYPE: DNA
```

```
<213> ORGANISM: Artificial Sequence
<220> FEATURE:
<223> OTHER INFORMATION: SEQ ID NO:7 - Synthetic

<400> SEQUENCE: 7
atggccctgc ctgtgacagc cctgctgctg cctctggctc tgctgctgca tgccgctaga      60
cccatccaga tgacacagac tacatcctcc ctgtctgcct ctctgggaga cagagtcacc     120
atcagttgca gggcaagtca ggacattagc aattttttaa actggtatca gcagaaacca     180
gatggaactg ttaaactcct gatctactac acatcaagat tacattctgg agtcccatca     240
aggttcagtg gcagtgggtc tggaacagat ttttctctca ccattagcaa actggagcaa     300
gaagatattg ccacttactt ttgccaacag gtaatacgc ttccacttac gttcggcgct      360
gggacaaagt tggaacttaa aggtggtggt ggttctggcg gcggcggctc cggaggagga     420
ggatcgctgc aacagtctgg acctgagttg gtgaagcctg gggcttcagt gaagatttcc     480
tgcaaggctt ctggatacac attcactgac tactacatga attgggtgaa gcttagccat     540
ggaaagagcc ttgagtggat tggagatatt gttcctaaca atggtgatac tacttacaac     600
cagaatttca gaggcaaggc cacattgact gtagacaagt cctccagcac agcctacatg     660
gagctccgca gcctgacatc tgaggactct gcagtctatt actgtgcaag attcagtaat     720
tacgtttacc cttttgacta ctggggccaa ggcaccacta tcacagtctc caccacgacg     780
ccagcgccgc gaccaccaac accggcgccc accatcgcgt cgcagcccct gtccctgcgc     840
ccagaggcgt gccggccagc ggcggggggc gcagtgcaca cgagggggct ggacttcgcc     900
tgtgatatct acatctgggc gcccttggcc gggacttgtg gggtccttct cctgtcactg     960
gttatcaccc tttactgcaa acggggcaga aagaaactcc tgtatatatt caaacaacca    1020
tttatgagac agtacaaac tactcaagag gaagatggct gtagctgccg atttccagaa     1080
gaagaagaag aggatgtga actgagagtg aagttcagca ggagcgcaga cgcccccgcg     1140
taccagcagg gccagaacca gctctataac gagctcaatc taggacgaag agaggagtac    1200
gatgttttgg acaagagacg tggccgggac cctgagatgg ggggaaagcc gagaaggaag    1260
aaccctcagg aaggcctgta caatgaactg cagaaagata agatggcgga ggcctacagt    1320
gagattggga tgaaaggcga gcgccggagg ggcaaggggc acgatggcct ttaccagggt    1380
ctcagtacag ccaccaagga cacctacgac gcccttcaca tgcaggccct gccccctcg    1439
```

ANTI-ROBO1 CAR-T CELL, AND PREPARATION AND APPLICATION THEREOF

This application is a national stage filing under 35 U.S.C. § 371 of International Application No. PCT/CN2016/092577, filed on Jul. 31, 2016, which claims the benefit of the filing date of Chinese Patent Application No. 201610237593.2, filed on Apr. 18, 2016, each of which is incorporated herein by reference.

REFERENCE TO AN ELECTRONIC SEQUENCE LISTING

The contents of the electronic sequence listing (Date of Creation: Nov. 6, 2018) are herein incorporated by reference in their entirety.

FIELD OF THE INVENTION

The present invention is related to the field of cellular drug for tumor therapy, particularly to an Anti-ROBO1 CAR-T cell, and preparation and application thereof.

BACKGROUND OF THE INVENTION

Human T lymphocytes recognize target cells through T cell receptors on their surfaces, this recognition is specific, that is, a T lymphocyte recognizes only target cells with specific antigens, and these specific antigens are presented to T lymphocytes through the action of special molecules after being processed in cells. These antigen-presenting molecules are either present on the surfaces of antigen presenting-cells or on the surfaces of target cells. There are at least two factors that cause T lymphocytes in vivo to be unable to recognize cancer cells very well: (1) cancer cells down-regulate the expression of antigen-presenting molecules, and (2) the binding affinities between the presented antigens and T cell receptors are weak. Although there are T lymphocytes highly specific to cancer cells in cancer patients, the number of T lymphocytes is too small to treat cancer. Based on this situation, scientists have proposed the concept of constructing a chimeric T cell receptor (now commonly referred to as a Chimeric antigen receptor). The Chimeric Antigen Receptor (CAR) is mainly composed of two parts, one end of which is located outside the cell that can specifically recognize an antigen on the surface of cancer cells, the other end of which is located in the cell that contains a signal activation element (such as a T cell receptor, Zeta chain), which acts to transmit signals to activate T cells. Therefore, the T-lymphocytes (CAR-T cells) expressing CAR can avoid the restrictions in recognition of the target cells by T cell, and therefore kill the target cancer cells.

Currently, clinical trials of CAR-T therapy are growing rapidly, most of which are evaluations of the treatment of B-cell malignancy. Most malignant B cell and normal B cells express the CD19 antigen, but other types of cells do not have CD19, so CD19 is a good therapeutic target. The compositions of CD19 CAR-T cells used in different clinical trials have been somewhat different, and clinical designs of CD19 CAR-T cells used in different clinical trials are also different. However, they were all reported to have significant effects. The response rates for the treatment of relapsed or refractory lymphocytic leukemia can reach 60-90%, with some patients achieving sustained remission, the longest of which was up to 2 years. Now it is not yet known that how long the sustained remission of the CD19 CAR-T treatment can achieve, but it is certain that this kind of immunotherapy has brought effects which were unattainable previously to some patients.

In addition to focusing on hematologic tumors, researchers also have been trying to extend CAR-T treatment to solid tumors. The results of the clinical trials have shown that GD2-specific CAR-T had certain effects on neuroblastoma, whereas there are no therapeutic effects of the aFR-specific CAR-T cells on ovarian cancer, CAIX-specific CAR-T cells on renal cell carcinoma, and PSMA-specific CAR-T cells on prostatic cancer. Carl H June et al. from the Pennsylvania University reported the treatment results of refractory and metastatic pancreatic ductal adenocarcinoma with mesothelin-specific CAR-T cells at the American Society of Clinical Oncology's annual meeting in 2015. The results showed that the patients had good tolerance for CAR-T cells and no cytokine syndrome occurred, CAR-T cells could be detected in the peripheral blood for a short period of time, and the conditions of 2 patients were stabilized. Therefore, the use of CAR-T for the treatment of solid tumors is still in an early stage, and there are still many problems to be solved.

Histopathological examination revealed that Robo1 was over expressed in various types of cancers, such as hepatocellular carcinoma, breast cancer, colon cancer, pancreatic cancer, prostate cancer, glioma, and the like. Studies by Ito et al. showed that Robo1 was abundantly expressed in hepatocellular carcinoma but only expressed in a small amount in normal tissues, and 84.7% of liver cancer tissue samples showed positive expression. Therefore, Robo1 can be used as a new hepatocyte tumor-associated antigen, which is a potential therapeutic and diagnostic target. Test results of GRONE et al. showed that the cancerous tissues of 80% of colon cancer patients had high expression level of Robo1 mRNA, in 45% of the patients, the expression levels were 4 times over those in normal tissues, and in 15% of the patients, the expression levels were 12 times over those in normal tissues. Therefore, Robo1 can provide a new potential target for the treatment of colon cancer. Compared with pancreatic ductal carcinoma to its surrounding benign tissue, He et al. found that Robo1 was up-regulated in cancer tissues, and this kind of up-regulation may be associated with lymphatic metastasis of pancreatic cancer cells. Studies by Huang et al also showed that Robo1 was related to the migration of colon cancer.

The extracellular domain of ROBO1 is composed of IG1-IG5 and FN3 domains, with the FN3 domain being proximal to the cell membrane. Therefore, the FN3 region is a preferred choice as an antigen when ROBO1 molecule is used as a target, so that when the CAR-T cells constructed by this method are in contact with tumor cells expressing ROBO1 molecule, the cells would be pulled together the closest to each other, and the killing effect would be better. The specific structure is shown in FIG. 1.

SUMMARY OF THE INVENTION

The main technical problem to be solved by the present invention is to provide an Anti-ROBO1 CAR-T cell, and preparation and application thereof, which is method for modifying and transforming T cells, so that the transformed T cells can specifically recognize and kill tumors, and the T cells prepared by the method have more efficient tumor killing activity.

In order to solve the above technical problem, one technical solution adopted by the present invention is to provide a CAR-T cell targeting the ROBO1 FN3 domain, wherein an SCFV-CD8™-4-1BB-CD3ζ fusion protein is expressed in the T cells.

In a preferred embodiment of the present invention, the CAR-T cell is manufactured by:

(1) synthesizing and amplifying the gene encoding the SCFV-CD8™-4-1BB-CD3ζ and cloning the gene encoding the SCFV-CD8™-4-1BB-CD3ζ fusion protein into a lentiviral expression vector;

(2) using a lentiviral envelop plasmid and the lentiviral expression vector of step (1) to infect a 293 T cell, packaging and preparing the virus;

(3) isolating and expanding human peripheral blood T lymphocytes and infecting the T lymphocytes with the lentivirus of step (2) to obtain the CAR-T cells expressing the ScFv-CD8™-4-1BB-CD3ζ fusion protein.

In a preferred embodiment of the present invention, the SCFV sequence molecule is expressed on a surface of the T lymphocyte, and the 4-1BB-CD3ζ molecule transmits the activating signal inside the T cell.

In a preferred embodiment of the present invention, the amino acid sequence of SCFV in the SCFV-CD8™-4-1BB-CD3ζ fusion protein is SEQ ID NO:5; and the amino acid sequence of CD8™ in the SCFV-CD8™-4-1BB-CD3ζ fusion protein is SEQ ID NO:1.

In a preferred embodiment of the present invention, the amino acid sequence of 4-1BB in the SCFV-CD8™-4-1BB-CD3ζ fusion protein is SEQ ID NO:2; wherein the 4-1BB in the SCFV-CD8™-4-1BB-CD3ζ fusion protein can be replaced by CD28 that has the amino acid sequence of SEQ ID NO:3.

In a preferred embodiment of the invention, the amino acid sequence of CD3ζ in the SCFV-CD8-4-1BB-CD3ζ fusion protein is SEQ ID NO:4; and the T cell is derived from human periphery blood T lymphocytes.

In a preferred embodiment of the invention, the amino acid sequence of the SCFV-CD8™-4-1BB-CD3ζ fusion protein is SEQ ID NO:6.

In a preferred embodiment of the invention, the CAR-T cell is used in the preparation anti-tumor drugs.

In a preferred embodiment of the invention, the CAR-T cell is used in preparation of the therapeutic drugs that target tumors with high expression of ROBO1.

The beneficial effects of the present invention are: in the Anti ROBO1 CAR-T cells of the present invention, and in the preparation and application thereof, ROBO1 antibody is used for the construction of CART cells, and the ROBO1 molecule is proposed as target antigen, and the Anti ROBO1 CART cells are used to kill tumor cells. In addition, the Anti ROBO1 CART cells are used as a cellular drug for the treatment of tumor diseases, which can be used for the treatment of tumors with high expression levels of ROBO1 molecules.

BRIEF DESCRIPTION OF THE DRAWINGS

In order to more clearly illustrate the technical solutions in the embodiments of the present invention, the figures used in the description of the embodiments will be briefly described below. It is obvious that the figures in the following description are only some embodiments of the present invention. For a person of ordinary skills in the art, other figures can be obtained based on these figures without any creative work. The figures include.

DETAILED DESCRIPTION OF THE INVENTION

The technical solutions in the embodiments of the present invention are clearly and completely described below. It is obvious that the described embodiments are only a part of the embodiments of the present invention, not all of the embodiments. Based on the embodiments of the present invention, all other embodiments are obtained by a person skilled in the art without any creative work is within the scope of the protection of the present invention.

Example 1: Preparation of a Lentiviral Expression Vector

Figure 1:
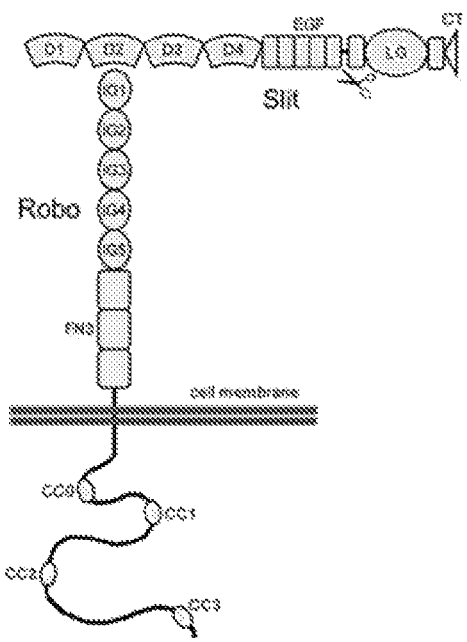
FIG. 1 illustrates a schematic diagram of the structure of the ROBO1 molecule of the present invention.
Figure 2:
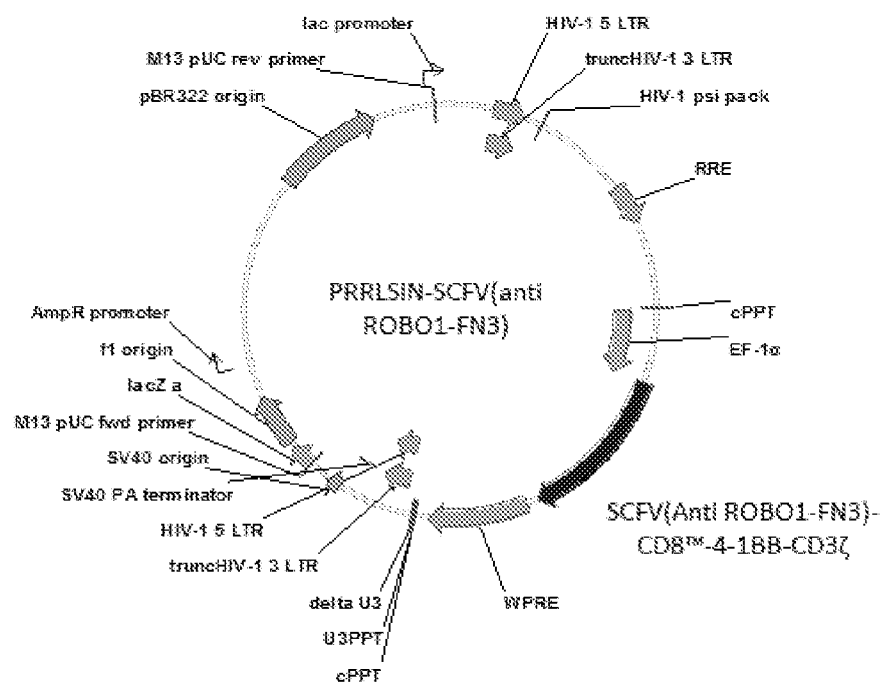
FIG. 2 illustrates a map of the PRRLSIN-SCFV (anti ROBO1-FN3) lentiviral plasmid vector of the present invention.

Synthesizing the gene encoding the SCFV (Anti ROBO1-FN3)-CD8-4-1BB-CD3ζ; wherein the gene sequence is SEQ ID NO:7, then the gene was ligated into the PRRSLIN vector by restriction enzyme and transformation, and the upstream of the gene is EP-1α promote. The vector was transformed into Stbl3 *Escherichia coli* strain and screened by ampicillin to obtain positive clones, then the plasmids were extracted and identified by restriction enzyme digestion, and PRRLSIN-SCFV (anti ROBO1-FN3) lentiviral transfection vector was obtain, the structure of which is as shown in FIG. 2.

Embodiment 2: Preparation of Lentivirus (1) Twenty-four hours before transfection, seeding 293T cells into 15 cm culture dishes at a cell density of approximately $8 \times 10^6$ cell per dish, which could ensure that the cells were at about 80% of confluence and evenly distributed in the culture dish during transfection.

(2) Prepare solution A and solution B

Solution A: 6.25 ml of 2×HEPES buffer (using 5 large dishes which are packed together could achieve the best effects).

Solution B: adding the following plasmids respectively, and mixing: 112.5 ug of pRRLSIN-EF-ROBO1 (target plasmid); 39.5 ug of pMD2.G (VSV-G envelop); 73 ug of pCMVR8.74 (gag, pol, tat, rev); 625 μl of 2M calcium ion solution. Total volume of solution A: 6.25 ml.

The solution B was mixed completely, and the solution A was added dropwise when the solution A was gently rocked, then let the solution sit for 5-15 minutes. The above mixed solution of A and B was gently rocked and added to the petri dish containing 293T cells dropwise, then the culture dish was gently shaken back and forth to distribute the mixture of DNA and calcium ions evenly. The culture dish was placed in an incubator to incubate for 16-18 hours (do not rotate the culture dish). Fresh medium was replaced and continued incubating, then the supernatant containing virus was collected after 48 hours and 72 hours, respectively. The supernatant containing virus was observed by fluorescence microscopy, more than 95% of the cells should show green fluorescence. The supernatant was centrifuged at 500 g for 10 minutes at 10° C., followed by being filtered with PES membrane (0.45 μm). Beckman Coulter Ultra-clear SW28 centrifuge tubes were sterilized with 70% ethanol, and sterilized under UV light for 30 minutes. The filtered supernatant containing lentivirus was transferred to a centrifuge tube. A layer of 20% sucrose was carefully spread on the bottom of the centrifuge tube (1 ml of sucrose was added per 8 ml of supernatant). The centrifuge tube was equilibrated with PBS, and centrifuged the supernatant at 25,000 rpm (82,700 g) for 2 hours at 4° C. The centrifuge tube was carefully taken out and poured off the supernatant, followed by being inverted to remove residual liquid. 100 μl of PBS was added in the centrifuge tube and sealed, then placed at 4° C. for 2 hours, gently rocked once per 20 minutes during the time, followed by being centrifuged for 1 minute (25° C.) at 500 g, and the virus supernatant was collected. After being cooled on ice, the virus supernatant was stored at −80° C.

Embodiment 3

Preparation of Anti ROBO1-FN3-CART Cells:
0.5 ml of blood was taken, and tested for pathogenic microorganisms rapidly to exclude microbial infections such as HBV, HCV, HDV and HEV, HIV-1/2, *Treponema pallidum* and parasites; 50 ml of blood was collected with heparin bottle (heparin anticoagulation) under sterile conditions, and immediately (4° C., within 24 hours) sent to the cell preparation laboratory to ensure that this process was free of pathogenic microbial contamination. After obtaining the patient's blood, the surface of the heparin bottle was wiped with an alcohol cotton ball for disinfection in the GMP preparation room, then the heparin bottle was placed in a biological safety cabinet. Two 50 ml centrifuge tubes were opened in advance, and the blood was transferred into the two 50 ml centrifuge tubes and tightened up. The above 50 ml centrifuge tubes filled with blood were placed in a centrifuge and centrifuged at 400 g (2000 rpm) for 10 min at room temperature, then the supernatant plasma was collected and the precipitate layer was removed after centrifugation. The collected autologous plasma was inactivated at 56° C. for 30 minutes. After being stood for 15 minutes at 4° C., the collected autologous plasma was centrifuged at 900 g for 30 min at 4° C. to take the supernatant for use. The enriched blood cells above were diluted to 30 ml/tube with physiological saline, and two new 50 ml centrifuge tubes were opened, then 15 ml of human lymphocyte separation liquid was added to each centrifuge tube. The diluted blood cell solution was slowly added to the centrifuge tube which contains the human lymphatic separation solution with a pipette, and tightened up. It was noted that the blood should be added to the upper layer of the lymphatic separation solution, and the interface of the human lymphatic separation solution should not be broken. The added blood cell solution was placed in a centrifuge which was adjusted to a minimum rate of rise and fall, then the added blood cell solution was centrifuged at 400 g (2000 rpm) for 20 min at room temperature. The middle white blood cell layer of two tubes was collected in a 15 ml sterile centrifuge tube, and 5 ml of physiological saline was added, and then washed twice (Centrifuging the collected middle white blood cell layer at 400 g for 10 minutes) to obtain peripheral blood mononuclear cells (PBMC). Complete growth medium was made, the concentration of V-VIVO15 added autologous AB (FBS) was 5%, the concentration of IL-2 was 40 ng/ml, and the isolated PBMC was diluted to $2×10^6$/ml with medium, then 50 ul was taken, and the T cells purity of PBMC was detected by flow cytometer on 0 day, Buffer1 was made that, 1% FBS was added to PBS and the beads were rocked for 30 s or manually shaken up and down for 5 min CD3/CD28 beads were taken out according to the ratio of beads to T cells of 3-1, and the beads were put in 1.5 ml EP tube, followed by adding 1 ml buffer1 to clean the beads. After that, The beads were suck from the EP tube for 1 min with magnet and washing solution was discarded, which was repeated twice, Then the beads were re-suspended to the original volume using the medium, and the cells and beads were mixed, followed by being added in a suitable culture bottle in $2×10^6$PBMC/ML. On the second day, the density of the cell was adjusted to $3-5×10^6$/ml, and the virus vector was added in the proportion of virus vector:cell of 1:5, meanwhile, 4 ug/ml and 40 ng/ml $IL^{-2}$ polybrene were added. After 4 hours, fresh complete medium was added, and the density of the cell was adjusted to $1×10^6$/ml to continuous culture. All the cells were centrifuged, and fresh medium was added to continuous culture. Half a volume change replaced per 2-3 days to maintain the density of the cell in $0.5-1×10^6$/ml. When the number of cells reached $10^9$ in the period of 10-12 days, the cells were centrifuged at 400 g for 5 min to get immune cells, followed by being washed twice with pre-cooled PBS (400 g, 5 min). The cells were count by a hemocytometer, and the cell group and the proportion of CART cells were detected by flow cytometer. The color change, cell density, and cell morphology of the medium were observed daily and recorded accordingly. The interleukin 2 which is required by total volume was added in the process of gradually expanding cultivation.

Embodiment 4

Figure 3:
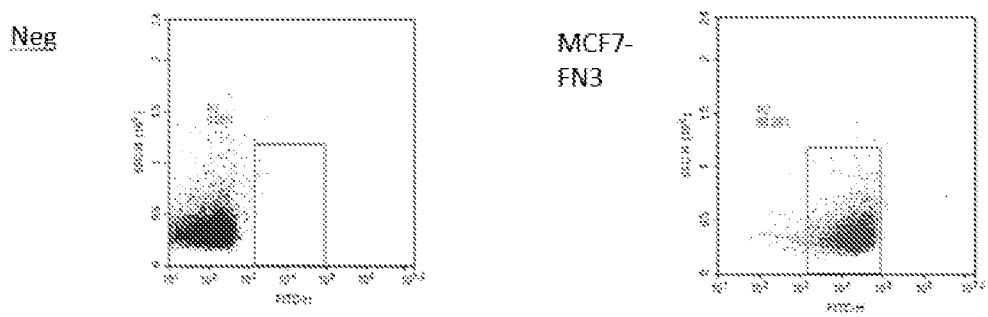
FIG. 3 illustrates a flow cytometry result of the MCF7/ROBO1 engineering cell line with high expression of ROBO1 of the present invention.

Construction and Detection of Engineering Cell Lines:
(1) Preparation of engineering cell line lentivirus with high expression Robo1 FN3 (the specific preparing method is also the method in the second embodiment);
(2) Infection of MCF cells: 500,000 MCF7 cells were inoculated in 6-well plates the day before infection. When the cells grow to 80% on the next day, 500 μl of packaged ROBO1 virus was added in a 6-well plate, meanwhile control cell (no virus added) was set, culture medium was changed after 12-16 hours, and then the positive cells of Robo1 were sorted by flow cytometer 3 days after infection;
(3) Detection of engineered cell lines: 20,000 cells were taken from the sorted positive cells of Robo1, followed by being centrifuged at 400 g for 5 min, then washed twice with pre-cooled PBS, and 2.5 μl of Robo1 antibody (Biolegend) was added and incubated in the dark for 20 min, after that, centrifuged and washed once with pre-cooled PBS, then the cells was re-suspended in 100 μl PBS, and the expression of Robo1 was detected by flow cytometer (see FIG. 3). The experimental results confirmed that the engineered cell lines were successfully constructed, which can be used as a target cell for subsequent killing experiments.

Embodiment 5

Activity Assay of Anti ROBO1-FN3-CART Cells In Vitro:
LDH release assay was used to detect the killing effect of Anti ROBO1-FN3-CART cells on engineered cell line MCF-1/ROBO1 and hepatoma cell line SMCC7721 with high Robo1-expressing. ELISA was used to detect LDH release.

(1) Adjusting the target cells to 5×10⁴/ml with RPMI-1640 medium containing 5% calf serum.

(2) Adding target cells to 96-well cell culture plates, and adding 100 μl to each well. Three effector cells naturally released control wells were only added 100 μl of culture solution without adding target cells.

(3) Adding 100 μl of effector cells to each well, and the ratio of effector cells to target cells was 50:1; 25:1; 10:1; 5:1; or 1:1. Natural release wells were only added 100 μl of culture medium without effector cells, and incubating the effector cells with the target cells for 6 hours, meanwhile, setting up three replicate wells for each experiment.

(4) Adding 10 μl Lysis Solution (10×) to the largest release well (positive control), and incubating for 45 min-60 min. Meanwhile, placing three replicate wells each experiment.

(5) Taking out 50 ul of the test sample and the control sample in the above 3 and 4 steps, respectively, and adding in the fresh 96-well microtiter plate, then adding the assay buffer and the substance mix, followed by being protected from light for 30 minutes.

(6) Adding 50 μl stop solution.

(7) Absorbance values were measured at 490 nm or 492 nm in an hour.

(8) Killing rate=experimental group LDH (OD)/Max LDH release group (OD).

(9) Calculation formula: Killing efficiency=(experimental-effector spontaneous−target spontaneous)/(target maximum-target spontaneous)×100%.

Figure 4:
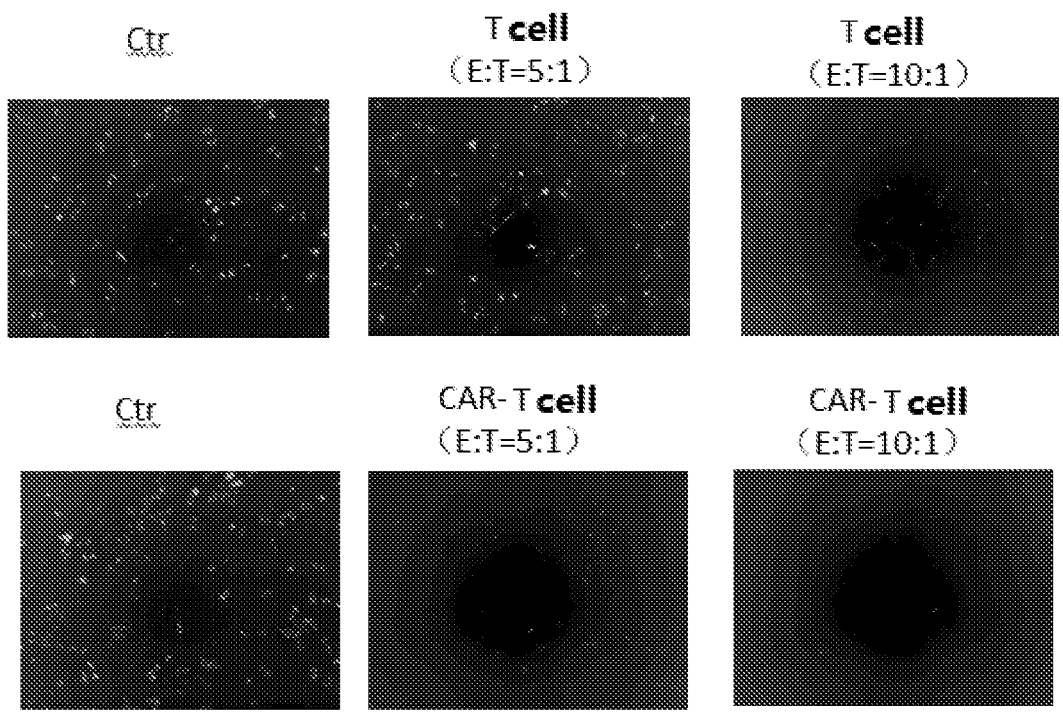
FIG. 4 illustrates a result of the CAR-T killing experiment in vitro of the present invention.
Figure 5:
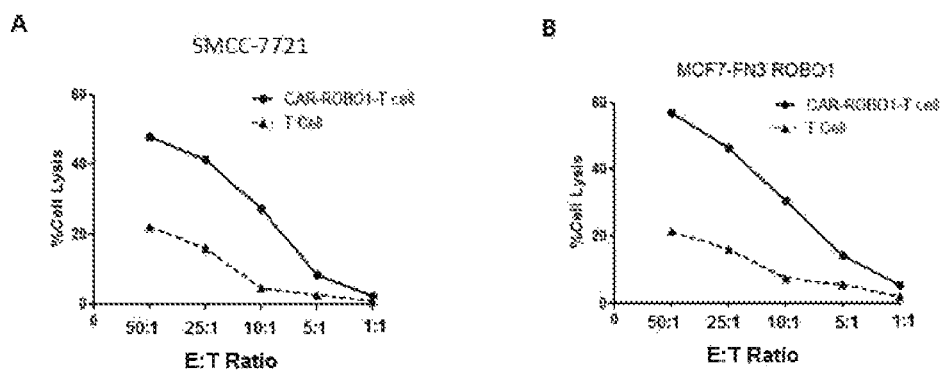
FIG. 5 illustrates a result of the killing effect of CAR-T cells in vitro under different effect-target ratio conditions of the present invention.

The results showed that the prepared Anti ROBO1-FN3 CART cells could significantly kill the target cell lines MCF-7/ROBO1 and SMCC7721 with high expression of ROBO1, and the different proportions of ROBO1 CAR-T and target cells were incubated for 4 hours, followed by being detected by ELISA experiment, which shown that the cell killing efficiency also increased (see FIG. 5), and microscopic imaging showed significant death of tumor cells (FIG. 4) with the increasing of the E:T ratio.

The above is only the embodiment of the present invention, and thus does not limit the scope of the patent of the present invention. Any equivalent structure or equivalent process transformation made by using the content of the description of the present invention, or other related technical fields were directly or indirectly applied, all the same was included in the scope of patent protection of the present invention.

SEQUENCE LISTING

The amino acid sequence of CD8 ™ SEQ ID NO: 1 is:
IYIWAPLAGTCGVLLLSLVITLYC

The sequence of 4-1BB SEQ ID NO: 2 is:
KRGRKKLLYIFKQPFMRPVQTTQEEDGCSCRFPEEEEGGCEL

SEQUENCE LISTING

The sequence of CD28 SEQ ID NO: 3 is:
RSKRSRLLHSDYMNMTPRRPGPTRKHYQPYAPPRDFAAYRS

The molecular sequence of CD3ζ SEQ ID NO: 4 is:
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR The sequence of SCFV (Anti ROBO1-FN3) SEQ ID NO: 5 is:
IQMTQTTSSLSASLGDRVTISCRASQDISNFLNWYQQKPDGTVKLLIYYT
SRLHSGVPSRFSGSGSGTDFSLTISKLEQEDIATYFCQQGNTLPLTFGAG
TKLELKGGGGSGGGGSGGGGSLQQSGPELVKPGASVKISCKASGYTFTDY
YMNWVKLSHGKSLEWIGDIVPNNGDTTYNQNFRGKATLTVDKSSSTAYME
LRSLTSEDSAVYYCARFSNYVYPFDYWGQGTTITVS The sequence of SCFV (Anti ROBO1-FN3)-CD8 ™-4-1BB-CD3ζ fusion protein SEQ ID NO: 6 is:
MALPVTALLLPLALLLHAARPIQMTQTTSSLSASLGDRVTISCRASQDIS
NFLNWYQQKPDGTVKLLIYYTSRLHSGVPSRFSGSGSGTDFSLTISKLEQ
EDIATYFCQQGNTLPLTFGAGTKLELKGGGGSGGGGSGGGGSLQQSGPEL
VKPGASVKISCKASGYTFTDYYMNWVKLSHGKSLEWIGDIVPNNGDTTYN
QNFRGKATLTVDKSSSTAYMELRSLTSEDSAVYYCARFSNYVYPFDYWGQ
GTTITVSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQE
EDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRR
GKGHDGLYQGLSTATKDTYDALHMQALPPR The nucleotide sequence SCFV (Anti ROBO1-FN3)-CD8 ™-4-1BB-CD3ζ fusion protein SEQ ID NO: 7 is:
ATGGCCCTGCCTGTGACAGCCCTGCTGCTGCCTCTGGCTCTGCTGCTGCA
TGCCGCTAGACCCATCCAGATGACACAGACTACATCCTCCCTGTCTGCCT
CTCTGGGAGACAGAGTCACCATCAGTTGCAGGGCAAGTCAGGACATTAGC
AATTTTTTAAACTGGTATCAGCAGAAACCAGATGGAACTGTTAAACTCCT
GATCTACTACACATCAAGATTACATTCTGGAGTCCCATCAAGGTTCAGTG
GCAGTGGGTCTGGAACAGATTTTTCTCTCACCATTAGCAAACTGGAGCAA
GAAGATATTGCCACTTACTTTTGCCAACAGGGTAATACGCTTCCACTTAC
GTTCGGCGCTGGGACAAAGTTGGAACTTAAAGGTGGTGGTGGTTCTGGCG
GCGGCGGCTCCGGAGGAGGAGGATCGCTGCAACAGTCTGGACCTGAGTTG
GTGAAGCCTGGGGCTTCAGTGAAGATTTCCTGCAAGGCTTCTGGATACAC
ATTCACTGACTACTACATGAATTGGGTGAAGCTTAGCCATGGAAAGAGCC
TTGAGTGGATTGGAGATATTGTTCCTAACAATGGTGATACTACTTACAAC
CAGAATTTCAGAGGCAAGGCCACATTGACTGTAGACAAGTCCTCCAGCAC
AGCCTACATGGAGCTCCGCAGCCTGACATCTGAGGACTCTGCAGTCTATT
ACTGTGCAAGATTCAGTAATTACGTTTACCCTTTTGACTACTGGGGCCAA
GGCACCACTATCACAGTCTCCACCACGACGCCAGCGCCGCGACCACCAAC
ACCGGCGCCCACCATCGCGTCGCAGCCCCTGTCCCTGCGCCCAGAGGCGT
GCCGGCCAGCGGCGGGGGGCGCAGTGCACACGAGGGGGCTGGACTTCGCC
TGTGATATCTACATCTGGGCGCCCTTGGCCGGGACTTGTGGGGTCCTTCT
CCTGTCACTGGTTATCACCCTTTACTGCAAACGGGGCAGAAAGAAACTCC
TGTATATATTCAAACAACCATTTATGAGACCAGTACAAACTACTCAAGAG
GAAGATGGCTGTAGCTGCCGATTTCCAGAAGAAGAAGAAGGAGGATGTGA
ACTGAGAGTGAAGTTCAGCAGGAGCGCAGACGCCCCCGCGTACCAGCAGG
GCCAGAACCAGCTCTATAACGAGCTCAATCTAGGACGAAGAGAGGAGTAC
GATGTTTTGGACAAGAGACGTGGCCGGGACCCTGAGATGGGGGGAAAGCC
GAGAAGGAAGAACCCTCAGGAAGGCCTGTACAATGAACTGCAGAAAGATA
AGATGGCGGAGGCCTACAGTGAGATTGGGATGAAAGGCGAGCGCCGGAGG
GGCAAGGGGCACGATGGCCTTTACCAGGGTCTCAGTACAGCCACCAAGGA
CACCTACGACGCCCTTCACATGCAGGCCCTGCCCCCTCG

---

The invention claimed is:

1. An isolated anti-Roundabout-like protein 1 (ROBO1) CAR-T cell comprising a nucleic acid sequence encoding an anti-ROBO1-ScFv-CD8-4-1 BB-CD3ζ fusion protein, wherein the ScFv portion of the fusion protein is expressed on a surface of the CAR-T cell and the 4-1 BB-CD3ζ portion of the fusion protein is expressed inside the CAR-T cell; wherein the amino acid sequence of the anti-ROBO1-ScFv-CD8-4-1 BB-CD3ζ fusion protein is SEQ ID NO:6.

2. The anti-ROBO1-ScFv CAR-T cell of claim 1, wherein the T cell is isolated from human periphery blood T lymphocytes.

3. The anti-ROBO1 CAR-T cell of claim 1, wherein the anti-ROBO1 CAR-T cell is administered for treatment of a tumor.

4. The anti-ROBO1 CAR-T cell of claim 3, wherein the tumor is characterized by high expression level of ROBO1.

* * * * *